United States Patent

Akbaev et al.

[11] 4,016,272
[45] Apr. 5, 1977

[54] ANTHELMINTIC THIODIPHENYLAMINE CUPRIC CHLORIDE COMPLEX SALT

[76] Inventors: Abdi Akbaev, perculor Sonkulsky; Vera Vasilievna Ezhova, ulitsa Krupskoi, 55, kv. 6, both of, Frunze, U.S.S.R.

[22] Filed: Mar. 20, 1975

[21] Appl. No.: 560,140

Related U.S. Application Data

[63] Continuation of Ser. No. 482,893, June 25, 1974, abandoned, which is a continuation of Ser. No. 319,049, Dec. 27, 1972, abandoned.

[52] U.S. Cl. .............................. 424/245; 424/247
[51] Int. Cl.$^2$ ................ A61K 31/555; A61K 31/54
[58] Field of Search ...................... 260/242, 243 A; 424/245

[56] References Cited
OTHER PUBLICATIONS

Sakinkova – Chem. Abst. vol. 77 (1972), p. 299u (abst. of 1969 article).
Kuchkarov – Chem. Abst. vol. 72 (1970), p. 65179w.

*Primary Examiner*—Sam Rosen
*Attorney, Agent, or Firm*—Holman & Stern

[57] ABSTRACT

A complex salt of a thiodiphenylamine cupric chloride of the formula:

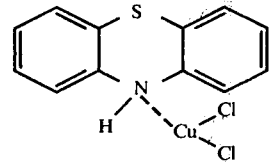

The process for producing said salt comprises reacting an aqueous solution of cupric chloride with thiodiphenylamine in a stoichiometric ratio of said cupric chloride and the thiodiphenylamine; the pH is from 2 to 2.5 and the temperature within the range of from 10° to 90° C. The precipitate of the desired product is separated from the mother liquor and dried. In order to reduce the acidity of the product being produced, the solution may be neutralized, prior to the separation of the precipitate, with a sodium or potassium carbonate or hydroxides of the said metals to a pH of from 7 to 8.

The complex salt of thiodiphenylamine cupric chloride possesses pharmacological activity and is useful in veterinary medicine as a helminthicide for treating helminth infestation diseases of farm animals. In addition, said salt may be used in agriculture as an insecto-fungicide.

4 Claims, No Drawings

ANTHELMINTIC THIODIPHENYLAMINE CUPRIC CHLORIDE COMPLEX SALT

This is a continuation of application Ser. No. 482,893 filed June 25, 1974 which in turn is a Rule 60 Continuation of Ser. No. 319,094 filed Dec. 27, 1972, both now abandoned.

The present invention relates to a novel compound, viz. a complex salt of thiodiphenyiamine cupric chloride, This salt, according to the invention, has the following formula:

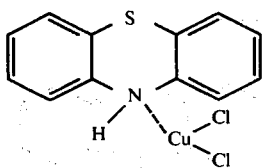

Said salt is a fine-crystalline powder, black or dark-brown in color, odoriess, slightly soluble in water (up to 2-2.5%), almost insoluble in organic solvents (up to 0.02% in ethanol, 0.1% in benzene, 0.02% in carbon tetrachloride) and well-soluble in mineral acids upon heating.

The complex salt of thiodiphenylamine cupric chloride possesses a pharmacological activity and is useful in veterinary medicine as a helminthicide for treating helminth infestation diseases such as nematodiases and cestodiasis in farm animals. In addition, said salt may be employed in agriculture as an insecto-fungicide.

According to the present invention, the complex salt of thiodiphenylamine cupric chloride is produced by reacting an aqueous solution of cupric chloride with thiodiphenylamine in a stoichiometric ratio between the cupric chloride and the thiodiphenylamine at a pH value of from 2 to 2.5 and a temperature within the range of from 20° to 80° C, preferably 60° to 70° C.

In order to increase the desired product yield it is advantageous to employ a concentrated (42–51%) aqueous solution of cupric chloride.

To lower the desired product acidity, it is advisable, prior to the separation of said product from the mother liquor, to neutralize said mother liquor at a temperature of 10° to 30° C with sodium carbonate, potassium carbonate, or hydroxides of said metals to a pH of 7–8.

As it has been mentioned hereinabove that the complex salt of thiodiphenylamine cupric chloride of the present invention possesses a pharmacological activity and is useful in veterinary medicine as a helminthicide for treating helminth infestation diseases such as nematodiases and cestodiasis in farm animals, for example sheep, goats, cows, chicken, rabbits, deer. etc. Said class of diseases also involves such diseases as moniea-sis, avitelliasis, habertiasis, gemoniasis, ascariasis, nem-atodiasis, strengliasis, and the like.

The helminthicide may be administered as a fine-crystalline powder of the said complex salt added in feeds for farm animals. In addition, said helminithicide may be used in the form of tablets comprising 100% of the active principle, viz. thiodiphenylamine cupric chloride complex salt. In both cases, i.e. powder and tablets, the helminthicide is to be administered perorally at a ratio of 0.1–0.3 g of the preparation per 1 kg of body weight of an animal.

Another form of the helminthicide is an aqueous suspension of said salt. In this case the preparation comprises an active principle in combination with 100 to 250 ml of water and is administered perorally at a ratio of 0.1 to 0.3 g of the active principle per 1 kg of body weight of the animal.

This novel helminthicide may be stored for long periods (over 5 years) at room temperature without loosing its activity.

The helminthicide action has been studied in laboratory and field conditions on sheep, cows, and other farm animals of different age and having various helminth infestation diseases. The course of treatment comprises a single oral administration of the preparation in spring and a repeated single administration in autumn. The preparation efficiency is 95 to 100% for the cured animals. The lethal dose $LD_{50}$ of the preparation is 1,000 g/kg and $LD_{100}$ is 1,200 g/kg for all varieties of farm animals.

Unlike the majority of the prior art helminthicides (phenothizaine, tin arsenate, piperazine, phenosal, naphthonone, and the like), the novel preparation of the present invention is highly efficient for curing various helminth infestation diseases in pre-imaginal and imaginal forms. The known preparations are efficient only in respect to the imaginal forms of certain helminth infestation diseases. The novel preparation based on thiodiphenylamine cupric chloride complex salt is not toxic and is convinient in use. In addition, it enhances productivity of farm animals with in respect to meat, milk, and wool.

For better understanding of the present invention the following specific examples of performing the process for producing the complex salt of thiodiphenylamine cupric chloride are given hereinbelow.

EXAMPLE 1

85 g of cupric chloride are dissolved in 100 ml of water. The solution is then added to 73 g of thiodiphenylamine powder and the mixture is stirred at a temperature of 30° C for a period of 2 hours at the pH = 2. The completion of the reaction is determined by the constancy of copper concentration in the solution and the uniformity of the precipitated crystals of the complex salt of thiodiphenylamine cupric chloride.

When equilibrium is attained in the reaction, the precipitate is filtered off to separate it from the mother liquor and is dried at a temperature of 50° C. 93 g of a black fine-crystalline salt are thus obtained which corresponds to the yield of 68% of the theoretical.

According to the chemical analysis date, the resulting salt contains 22.27% by weight of chlorine, 10.6% by weight of sulphur, 3.3% by weight of nitrogen, and 19% by weight of copper, which corresponds to the formula $CuCl_2 \cdot S(C_6H_4)_2NH$. This copper complex salt has the molecular weight of 333.72, a specific gravity of 2.556 g/cm$^3$, and a melting point of 115° C.

EXAMPLE 2

89 g of cupric chloride are dissolved in 100 ml of water. The solution is then added to 85 g of thiodiphenylamine powder and the mixture is stirred at temperature 60° C at pH 2.3 for a period of 3 hours.

When equilibrium is attained in the chemical reaction, the solution is cooled to a temperature of 30° C and neutralized with sodium carbonate to a pH = 8. The precipitate of thiodiphenylamine cupric chloride complex salt is then separated from the mother liquor by filtration and dried at a temperature of 80° C 95 g of a black fine-crystalline salt are thus obtained which corresponds to a yield of 70% of the theoretical.

Chemical analysis of the salt yields results similar to those of Example 1.

EXAMPLE 3

102 g of cupric chloride are dissolved in 100 ml of water. The solution is then added to 90 g of thiodiphenylamine and the mixture is stirred at a temperature of 90° C at pH = 2.5 for 2 hours.

When equilibrium of the chemical reaction is attained, the solution is cooled to a temperature of 30° C and neutralized with sodium hydroxide to a pH = 7.5. The precipitate of the complex salt of thiodiphenylamine cupric chloride is then separated from the mother liquor by filtration and dried at a temperature of 70° C. 100 g of a black fine-crystalline salt are thus obtained which corresponds to a yield of 75% of the theoretical.

Chemical analysis of the salt gives results similar to those of Example 1.

EXAMPLE 4

30 g of cupric chloride are dissolved in 100 ml of water. THe solution if then added to 20 g of thiodiphenylamine powder and the mixture is stirred at a temperature of 10° C at pH = 2.1 for 5 hours.

When equilibrium is attained in the chemical reaction, the solution is neutralized at said temperature with potassium carbonate to a pH = 7. The precipitate of the complex salt of thiodophenylamine cupric chloride is then separated from the mother liquor by filtration and dried at a temperature of 20° C. 30 g of a dark-brown fine-crystalline salt are thus obtained, which corresponds to a yield of 60% of the theoretical.

Chemical analysis shows results similar to those of Example 1.

We claim:

1. A method of treating helminth infestation diseases in animals which comprises administering to an animal from 0.1 to 0.3 gm per 1 kg of body weight of said animal of a complex salt of thiodiphenylamine cupric chloride of the formula:

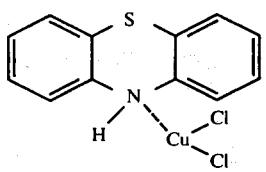

2. The method of claim 1 wherein said salt is administered in the form of a crystalline powder.

3. The method of claim 1 wherein said salt is administered in tablet form.

4. The method of claim 1 wherein said salt is administered in the form of an aqueous suspension.

* * * * *